(12) United States Patent
Kim et al.

(10) Patent No.: US 10,786,623 B2
(45) Date of Patent: Sep. 29, 2020

(54) CHEMICAL FLUID INJECTION DEVICE

(71) Applicant: EOFLOW CO., LTD., Seongnam-si, Gyeonggi-do (KR)

(72) Inventors: Jesse Jaejin Kim, Seongnam-si (KR); Jong Ook Jeong, Seongnam-si (KR); Seung Ha Kim, Goyang-si (KR)

(73) Assignee: EOFlow Co., Ltd., Seongnam-si, Gyeonggi-do (KR)

( * ) Notice: Subject to any disclaimer, the term of this patent is extended or adjusted under 35 U.S.C. 154(b) by 0 days.

(21) Appl. No.: 16/128,323

(22) Filed: Sep. 11, 2018

(65) Prior Publication Data

US 2019/0009020 A1    Jan. 10, 2019

Related U.S. Application Data

(63) Continuation of application No. PCT/KR2017/002577, filed on Mar. 10, 2017.

(30) Foreign Application Priority Data

Mar. 11, 2016 (KR) .................. 10-2016-0029679

(51) Int. Cl.
*A61M 5/158* (2006.01)
*A61M 5/00* (2006.01)
*A61M 5/142* (2006.01)

(52) U.S. Cl.
CPC .............. *A61M 5/158* (2013.01); *A61M 5/00* (2013.01); *A61M 5/142* (2013.01); *A61M 2005/14252* (2013.01); *A61M 2005/1585* (2013.01); *A61M 2005/1588* (2013.01); *A61M 2205/0216* (2013.01); *A61M 2205/18* (2013.01); *A61M 2205/33* (2013.01); *A61M 2205/50* (2013.01)

(58) Field of Classification Search
CPC .......... A61M 5/158; A61M 2005/1585; A61M 2005/1588; A61M 2205/18
USPC ................................................... 604/136, 117
See application file for complete search history.

(56) References Cited

U.S. PATENT DOCUMENTS

| 5,571,133 | A | 11/1996 | Yoon | |
|---|---|---|---|---|
| 6,171,276 | B1 * | 1/2001 | Lippe | ...................... A61M 5/20 128/DIG. 1 |

(Continued)

FOREIGN PATENT DOCUMENTS

| EP | 1 535 637 A1 | 6/2005 |
|---|---|---|
| EP | 1 646 412 A1 | 4/2006 |

(Continued)

OTHER PUBLICATIONS

Office Action dated Apr. 30, 2018 in Korean Patent Application No. 10-2016-0029679; 10 pages.

(Continued)

*Primary Examiner* — Brandy S Lee
*Assistant Examiner* — Nidah M Hussain
(74) *Attorney, Agent, or Firm* — Knobbe, Martens, Olson & Bear, LLP

(57) ABSTRACT

The disclosed technology generally relates to medical devices, and more particularly to a chemical fluid injection device. In an aspect, a chemical fluid injection device is configured to recognize whether a needle attached to a needle holder is inserted into a patient by sliding the needle holder and sensing whether the needle holder is adjacent to a needle penetration hole.

9 Claims, 12 Drawing Sheets

(56) References Cited

U.S. PATENT DOCUMENTS

| | | | |
|---|---|---|---|
| 7,686,787 B2 | 3/2010 | Moberg et al. | |
| 8,998,842 B2 | 4/2015 | Lauchard et al. | |
| 9,222,996 B2 | 12/2015 | Fujimoto et al. | |
| 9,522,229 B2* | 12/2016 | Sonderegger | A61M 5/3287 |
| 2003/0216767 A1* | 11/2003 | List | A61B 5/150412 |
| | | | 606/181 |
| 2008/0051718 A1 | 2/2008 | Kavazov et al. | |
| 2009/0221914 A1* | 9/2009 | Barrett | A61M 5/14216 |
| | | | 600/431 |
| 2012/0221036 A1 | 8/2012 | Ahmann et al. | |
| 2013/0296807 A1 | 11/2013 | Lintern et al. | |
| 2015/0190575 A1 | 7/2015 | Lauchard et al. | |
| 2016/0089056 A1* | 3/2016 | Limaye | A61M 5/46 |
| | | | 600/365 |
| 2017/0224935 A1 | 8/2017 | Hoffmann et al. | |

FOREIGN PATENT DOCUMENTS

| | | |
|---|---|---|
| EP | 2 331 190 B1 | 10/2012 |
| JP | 2009-525111 | 7/2009 |
| JP | 2010-501281 | 1/2010 |
| JP | 2013-533069 | 8/2013 |
| KR | 10-0516727 B1 | 9/2005 |
| KR | 10-1422858 B1 | 7/2014 |
| KR | 10-1550203 B1 | 9/2015 |
| KR | 10-2016-0008508 A | 6/2017 |
| WO | WO 2015-187797 | 12/2015 |
| WO | WO 2016/022865 A1 | 2/2016 |
| WO | WO 2017-155333 | 9/2017 |

OTHER PUBLICATIONS

Office Action dated Oct. 19, 2017 in Korean Patent Application 10-2016-0029679; 11 pages.
Office Action in Korean Application No. 10-2016-0029679, dated Oct. 19, 2017.
Final Office Action in Korean Application No. 10-2016-0029679, dated Apr. 30, 2018.
International Search Report and Written Opinion from related PCT patent application No. PCT/KR2017/002577 dated Sep. 10, 2018 (6 pgs.), as well as English translation of ISR (5 pgs.); 11 pages total.
Office Action dated Aug. 6, 2019 in Japanese Patent Application No. 2018-548092; 11 pages.
Supplementary European Search Report dated Sep. 26, 2019 in European Patent Application No. 17 76 3594; 6 pages.

* cited by examiner

CHEMICAL FLUID INJECTION DEVICE

CROSS-REFERENCE TO RELATED APPLICATIONS

This application is a continuation of PCT Application No. PCT/KR2017/002577, filed on Mar. 10, 2017, which claims priority to Korean Patent Application No. KR 10-2016-0029679, filed on Mar. 11, 2016. Each of the above applications is incorporated herein by reference in its entirety.

BACKGROUND

Technical Field

The disclosed technology generally relates to medical devices, and more particularly to a chemical fluid injection device.

Description of the Related Technology

Chemical fluid injection devices such as insulin injection devices are used to inject a chemical fluid into the body of a patient, and such devices are used most by ordinary people such as patients themselves, caregivers, and/or medical professionals such as doctors or nurses. In addition, since some chemical fluids injected using such chemical fluid injection devices, e.g., insulin, may be administered repeatedly over an extended period of time, patients suffer from repeated pain because of repeated insertion of needles of the chemical fluid injection devices.

Many chemical fluid injection devices include a needle through which a chemical fluid is injected into the body, and since the needle has to be inserted into the body of a patient, patients inevitably feel pain. In addition, such pain caused by needle insertion may in turn cause patients to fear using the chemical fluid injection devices, and eventually may cause aversion to the chemical fluid injection devices. In addition, the fear of needle insertion may make it difficult for patients to objectively check whether a needle is sufficiently inserted into their body. Thus, although a needle is not sufficiently inserted, a patient may try to inject a chemical fluid.

SUMMARY OF CERTAIN INVENTIVE ASPECTS

Embodiments of the present disclosure aim to solve and/or overcome, among other problems, the above-described problems and/or limitations by providing a chemical fluid injection device configured to reduce pain and fear associated with the needle insertion and to enable clear recognition of needle insertion.

To achieve the above-described objectives among other objectives, in an aspect of the disclosed technology, a chemical fluid injection device includes a casing including a needle penetration hole. The device additionally includes a button exposed outside the casing. The device additionally includes a needle holder located in the casing and configured to be coupled to a needle. The needle holder faces the needle penetration hole and is configured to be driven toward the needle penetration hole by actuation or pressing of the button. The device additionally includes a sensor located in the casing. The sensor is configured to sense whether the needle holder is adjacent to the needle penetration hole. The device further includes a controller electrically connected to the sensor.

The sensor may include: a first sensing member adjacent to the needle penetration hole; and a second sensing member coupled to the needle holder and facing the first sensing member.

The chemical fluid injection may further include an alarm device electrically connected to the sensor and configured to generate an alarm when the needle holder is adjacent to the needle penetration hole.

The controller may include: a first processor configured to control injection of a chemical fluid through the needle; and a second processor configured to determine, using the sensor, whether the needle holder is adjacent to the needle penetration hole, and to perform injection of the chemical fluid using the first processor when the needle holder is adjacent to the needle penetration hole.

The chemical fluid injection device may further include: a spring between the button and the needle holder; and a guiding member provided in the casing and configured to support the needle holder.

In another aspect, a chemical fluid injection device includes a casing including a base in which a needle penetration hole is formed. The device additionally includes a needle holder located in the casing and configured to be coupled to a needle. The needle may or may not be attached to the needle holder, depending on whether the device is being used or not. The needle holder is configured to be driven toward the needle penetration hole. The device additionally includes a sensor located in the casing and configured to sense whether the needle holder is adjacent to the needle penetration hole. The device additionally includes a controller electrically connected to the sensor, wherein the needle holder may be apart from the base in a first state and may be adjacent to the needle penetration hole in a second state. The controller may be configured to determine whether the needle holder is adjacent to the needle penetration hole in the second state.

The sensor may include: a first sensing member adjacent to the needle penetration hole; and a second sensing member coupled to the needle holder and facing the first sensing member.

The chemical fluid injection may further include an alarm device electrically connected to the sensor and configured to generate an alarm when the needle holder is adjacent to the needle penetration hole in the second state.

The controller may include: a first processor configured to control injection of a chemical fluid through the needle; and a second processor configured to perform injection of the chemical fluid using the first processor when the needle holder is adjacent to the needle penetration hole in the second state.

The chemical fluid injection device may further include a spring configured to support the needle holder, wherein the needle holder may be configured to be driven toward the needle penetration hole by elasticity of the spring when the needle holder is switched from the first state to the second state.

The guiding member may include a second support configured to support a first support in the first state.

The devices according to the disclosed technology provide various advantages. As described above, according to embodiments of the present disclosure, the needle holder is slid at a time by elasticity of the spring such that the needle attached to the needle holder may be momentarily inserted into a patient.

Owing to this momentary insertion of the needle, the patient may feel relatively less pain and may develop relatively less fear of the needle.

Therefore, patients undergoing long-term administration of chemical fluids may develop less aversion to or fear of the chemical fluid injection device and may be provided with smooth administration of chemical fluids, thereby contributing to the treatment and/or health of the patients.

Whether the needle sufficiently protrudes and is inserted into a patient is checked by sensing the distance that the needle protrudes from the needle holder, instead of relying on the sense of the patient, and thus, the chemical fluid may be injected more accurately.

In addition, since the chemical fluid is injected only after the needle sufficiently protrudes, the patient may easily recognize exact timing of chemical fluid injection, and the chemical fluid may be exactly supplied to a target part.

DETAILED DESCRIPTION OF CERTAIN ILLUSTRATIVE EMBODIMENTS

Figure 1:
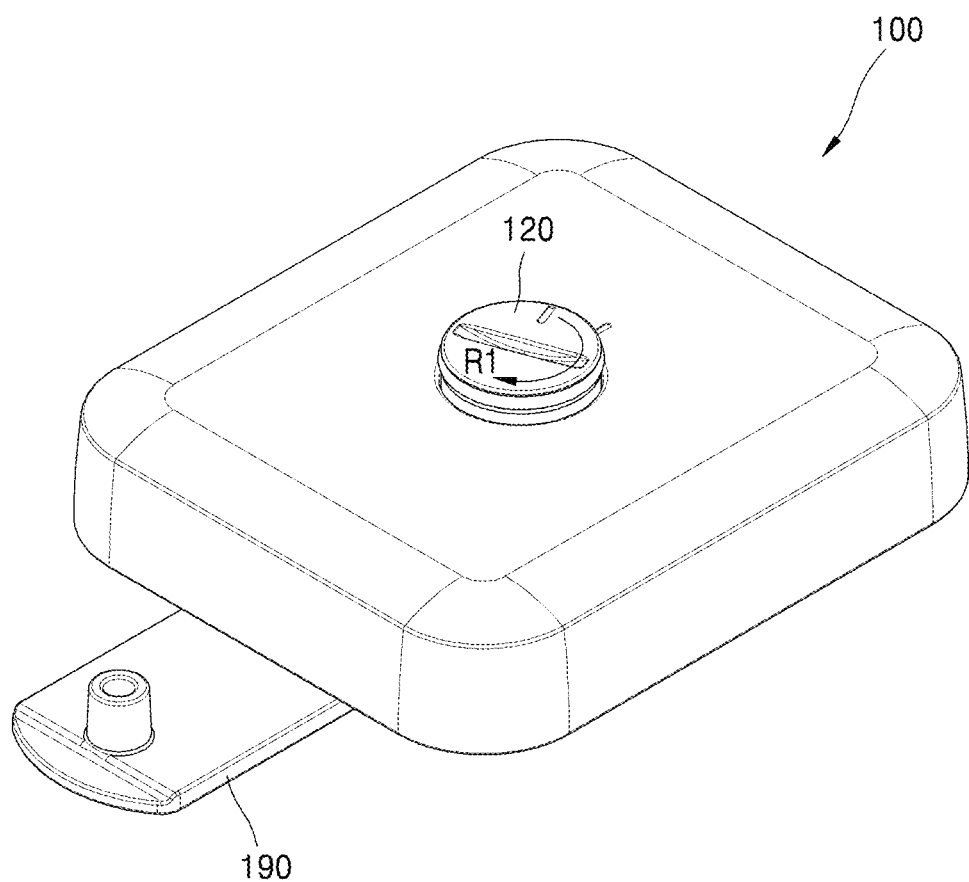
FIG. 1 is a perspective view illustrating a chemical fluid injection device, according to an embodiment.

The disclosed technology may include various embodiments and modifications, and certain embodiments thereof are illustrated in the drawings and will be described herein in detail. The effects and features of the present disclosure and the accomplishing methods thereof will become apparent from the following description of the embodiments taken in conjunction with the accompanying drawings. However, the present disclosure is not limited to the embodiments described below, and may be embodied in various modes.

Hereinafter, embodiments of the present disclosure will be described in detail with reference to the accompanying drawings. In the following description, like reference numerals will denote like elements, and redundant descriptions thereof will be omitted.

In the following descriptions of the embodiments, the terms of a singular form may include plural forms unless referred to the contrary.

It will be further understood that the terms "comprises" and/or "comprising" used herein specify the presence of stated features or elements, but do not preclude the presence or addition of one or more other features or elements.

It will be understood that when a film, a region, or an element is referred to as being "above" or "on" another film, region, or element, it can be directly on the other film, region, or element, or intervening films, regions, or elements may also be present.

The order of processes explained in one embodiment may be changed in a modification of the embodiment or another embodiment. For example, two consecutively described processes may be performed substantially at the same time or performed in an order opposite to the described order.

In the drawings, the sizes of elements may be exaggerated for clarity. In other words, since sizes and thicknesses of elements in the drawings are arbitrarily illustrated for convenience of explanation, the following embodiments are not limited thereto.

FIG. 1 is a perspective view illustrating a chemical fluid injection device, according to embodiments.

The chemical fluid injection device 100 according to the embodiment includes a button 120 exposed on a surface thereof and a needle cover assembly 190 on the other surface thereof.

The button 120 is exposed to a user such that the user may press, actuate and/or rotate the button 120. The needle cover assembly 190 is provided to protect a needle and may be separated when a user uses the chemical fluid injection device 100.

Figure 2:
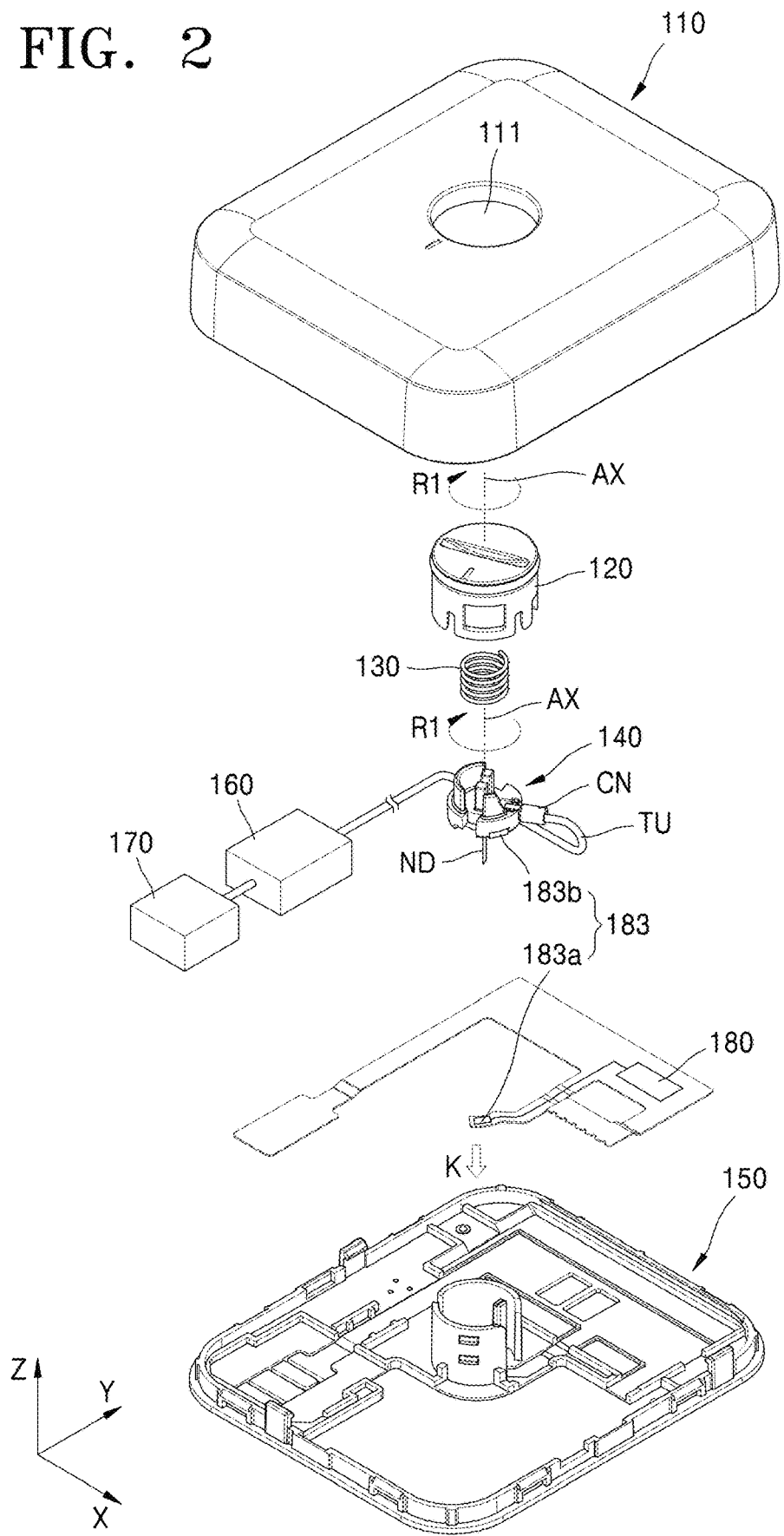
FIG. 2 is an exploded perspective view illustrating the chemical fluid injection device illustrated in FIG. 1.

Various components of the chemical fluid injection device 100 may be specifically configured as shown in FIG. 2, according to embodiments.

In an embodiment, the chemical fluid injection device 100 may include a casing, and the casing may include a first casing 110, e.g., an upper casing, and a second casing 150, e.g., a lower casing, coupled to each other.

The first casing 110 is exposed to a user even after the chemical fluid injection device 100 is attached to the body of the user, and an opening 111 is formed in a portion of the first casing 110. The button 120 may be inserted through the opening 111 and exposed to the user.

The button 120, a spring 130, a needle holder 140, a pump 160, a chemical fluid storage unit 170, a sensor 183, and a controller 180 may be located between the first casing 110 and the second casing 150, inside the casing.

Although not shown in the drawings, the chemical fluid storage unit 170 may include a reservoir configured to store a chemical fluid and a piston configured to eject the chemical fluid. However, the chemical fluid storage unit 170 is not limited thereto. For example, the chemical fluid storage unit 170 may include only the reservoir. The chemical fluid that may be stored may be a liquid containing medicine, e.g., insulin.

The chemical fluid storage unit 170 may be connected to the pump 160 via a fluid connection member such as a tube. The pump 160 is configured to pump the chemical fluid toward the needle holder 140, and a given amount of the chemical fluid may be pumped within a given pumping duration or period. The pump 160 may be electrically connected to a separate power source (not shown) and to the controller 180 which controls injection of the chemical fluid using the pump 160. The pump 160 may be configured to suction the chemical fluid from the chemical fluid storage unit 170 and to discharge the chemical fluid to the needle holder 140.

The pump 160 may be a suitable kind of pump capable of generating suction and discharge force using electricity. For example, any kind of pump such as a mechanical displacement micro-pump or an electromagnetic motion micro-pump may be used as the pump 160. The mechanical displace micro-pump may use motions of a fluid or a solid such as a gear or diaphragm to induce a pressure difference leading to flow of a fluid, and examples of the mechanical displacement micro-pump include a diaphragm displacement pump, a fluid displacement pump, and a rotary pump to name a few. The electromagnetic micro-pump may directly use electrical or magnetic energy for moving a fluid, and examples of the electromagnetic micro-pump include an electro hydrodynamic pump (EHD), an electro osmotic pump, a magneto hydrodynamic pump, and an electro wetting pump to name a few.

The pump 160 may be connected to the needle holder 140 through a tube TU and a connector CN. The tube TU connected to the pump 160 may be connected to the connector CN, and the connector CN may be connected to a needle ND while being supported by the needle holder 140. Therefore, the chemical fluid ejected from the pump 160 may be discharged through the needle ND after passing through the tube TU and the connector CN. To this end, the needle holder 140 is coupled to the needle ND.

The needle holder 140 faces the button 120, and the spring 130 may be located between the needle holder 140 and the button 120. The button 120, the spring 130, and the needle holder 140 may be aligned along an axis AX. The axis AX may be parallel to a Z-axis in the drawings.

In the embodiment shown in FIG. 2, the shape and/or arrangement of the chemical fluid storage unit 170 and the pump 160 as shown are meant to serve schematic illustrative purposes, and are not intended to limit to the illustrated shape and/or arrangement.

In addition, the sensor 183 may be located in the casing to sense whether the needle holder 140 is adjacent or within proximity to a needle penetration hole formed in the second casing 150. In an embodiment, the sensor 183 may sense whether the needle holder 140 makes contact with a base of the second casing 150 in a second state in which the needle protrudes outside a cover.

In some embodiments, the sensor 183 may include more than one member. For example, in the illustrative embodiment, the sensor 183 includes a first sensing member 183a adjacent to the needle penetration hole, and a second sensing member 183b coupled to the needle holder 140. The first sensing member 183a may be coupled to the second casing 150, e.g., mechanically and/or electrically coupled through a printed circuit board (PCB), and the first sensing member 183a and the second sensing member 183b may face each other. As shown in FIG. 2, the first sensing member 183a may be formed on a PCB e.g., field-programmable printed circuit board (FPCB) and may be electrically connected to the controller 180 through the FPCB.

Figure 3:
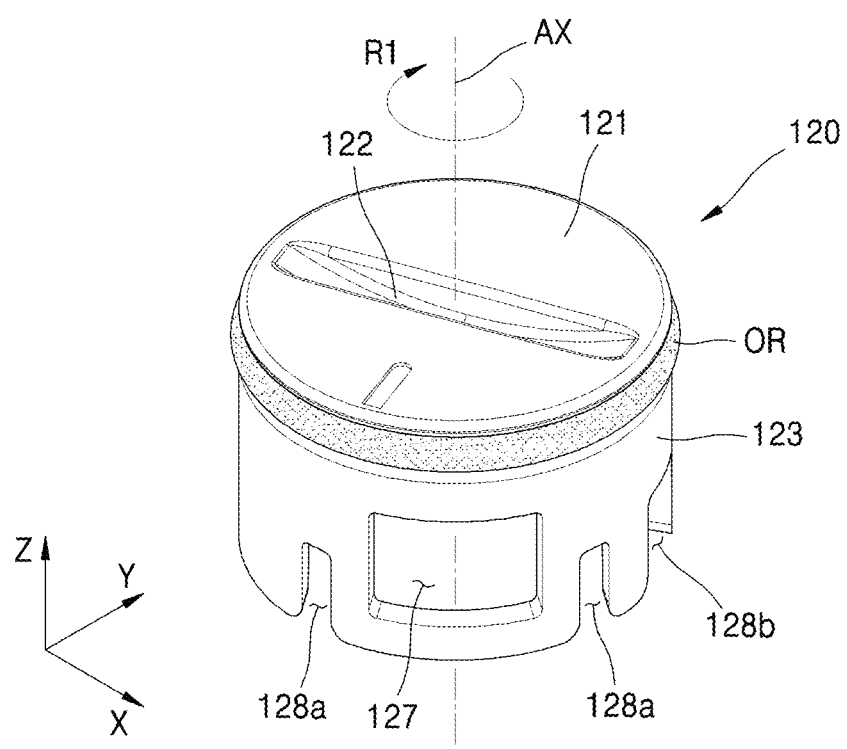
FIG. 3 is a perspective view illustrating a button, according to an embodiment.
Figure 4:
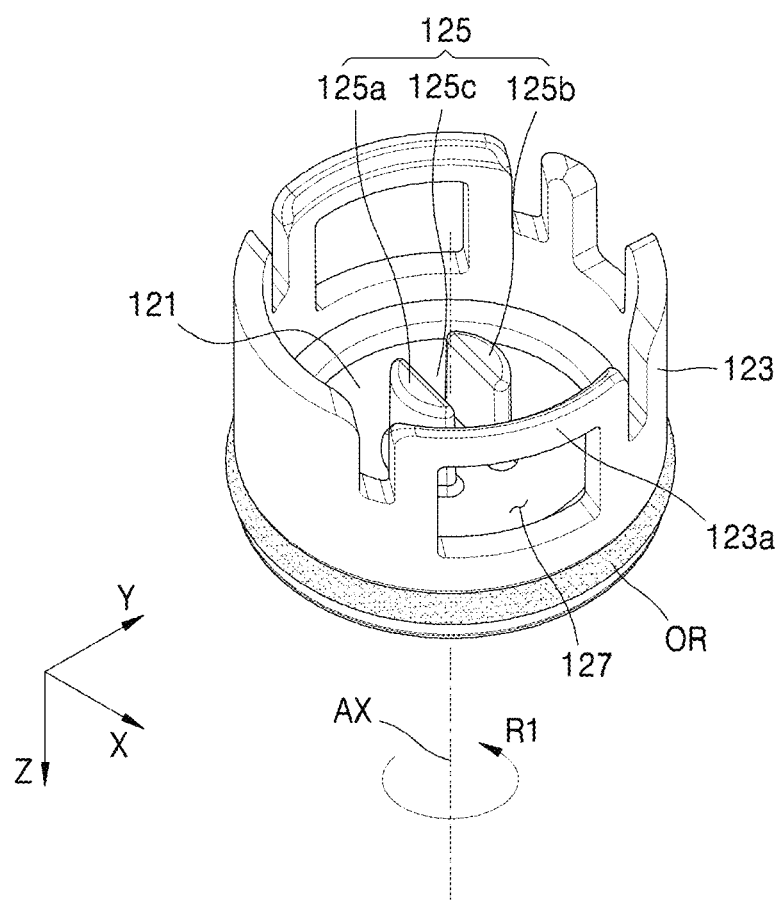
FIG. 4 is a bottom perspective view of the button illustrated in FIG. 3.

FIGS. 3 and 4 are a perspective view and a bottom perspective view, respectively, illustrating the button 120, according to an embodiment.

The button 120 may have an approximately cylindrical shape and may be rotatable about the axis AX in a rotation direction R1. A rotation groove 122 is formed in a Z-axis-direction surface 121 of the button 120 and has a shape and dimensions such that a user may easily rotate the button 120. For example, a user may easily rotate the button 120 by inserting his/her nail or a coil into the rotation groove 122.

The button 120 may have a cylindrical lateral side 123, and a ring member OR is fitted around about an upper end of the cylindrical lateral side 123. The ring member OR may be an O-ring, e.g., an elastomeric O-ring, and may prevent leakage of the chemical fluid between the button 120 and the opening 111 of the first casing 110. In addition, the ring member OR may provide a predetermined amount of resistance to pressing when a user presses the button 120, and/or may prevent the button 120 from easily popping up after being pressed.

As shown in FIGS. 3 and 4, coupling openings 127 may be formed in the lateral side 123. At least a pair of coupling openings 127 may be provided in symmetric portions of the lateral side 123. The coupling openings 127 may be located approximately in a middle portion of the lateral side 123 in the Z-axis direction, and accordingly coupling bands 123a may be formed on edges of the coupling openings 127. Stoppers (described later) may be coupled to the coupling openings 127, and separation of the button 120 may be prevented as the stoppers are caught on the coupling bands 123a. The coupling openings 127 may extend along an outer circumferential surface of the lateral side 123 in an X-Y plane to allow rotation of the button 120 in the rotation direction R1 in a state in which the button 120 is coupled to the stoppers.

First recesses 128a may be formed in portions of the lateral side 123 adjacent to the coupling openings 127. The first recesses 128a may be located on both sides of each of the coupling openings 127 to provide a given amount of elasticity when the coupling openings 127 are coupled to the stoppers.

A second recess 128b may be further formed in the lateral side 123, and when the button 120 is coupled to the needle holder 140, the connector CN may penetrate the lateral side 123 through the second recess 128b.

As shown in FIG. 4, a first coupling portion 125 may be provided on an inner side of the button 120, for example, a surface of the button 120 facing the needle holder 140. The first coupling portion 125 may be coupled to a second coupling portion (described infra including, e.g., in reference to FIGS. 5 and 5) of the needle holder 140. The first coupling portion 125 may include a first coupling protrusion 125a and a second coupling protrusion 125b protruding toward the needle holder 140 and facing each other at a distance from each other, and a gap 125c between the first coupling protrusion 125a and the second coupling protrusion 125b. It is not definitely necessary to fixedly couple the first coupling portion 125 to the second coupling portion (described below including, e.g., in reference to FIGS. 5 and 6). The first coupling portion 125 may be of any type as long as the first coupling portion 125 can engage with the second coupling portion as the button 120 is pressed by a user and can transmit rotation force of the button 120 to the needle holder 140 when the button 120 is rotated by the user.

Figure 5:
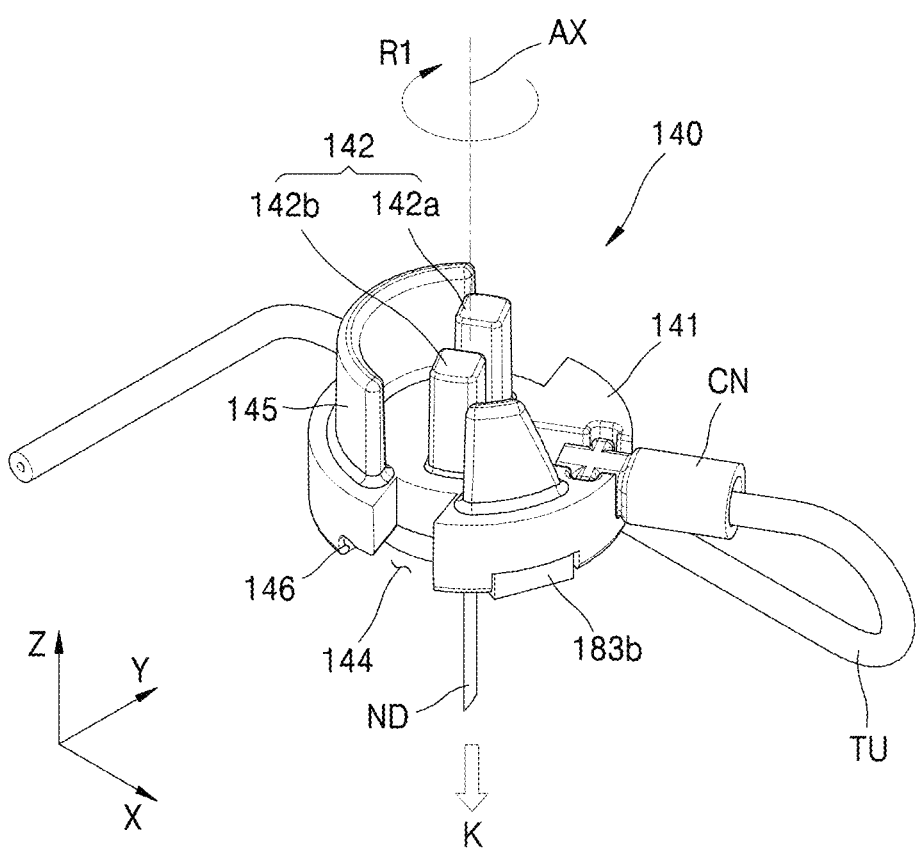
FIG. 5 is a perspective view illustrating a needle holder, according to an embodiment.
Figure 6:
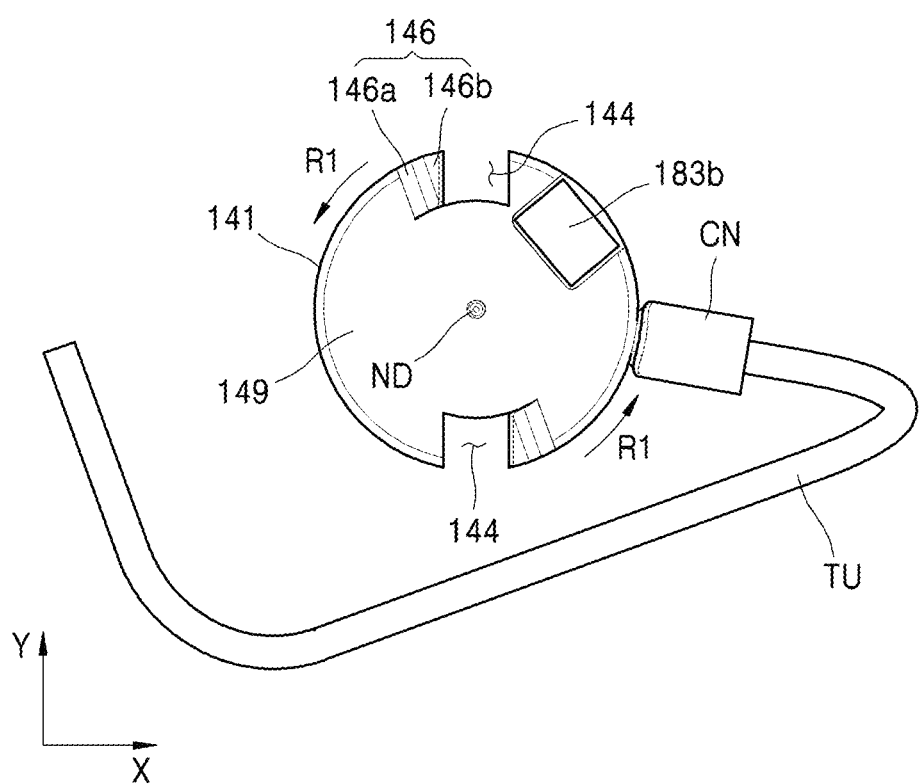
FIG. 6 is a bottom view of the needle holder illustrated in FIG. 5.

FIGS. 5 and 6 are a perspective view and a bottom perspective view, respectively, illustrating the needle holder 140, according to an embodiment.

According to the illustrated embodiment, the needle holder 140 includes a body 141 having an approximately disc shape for easy rotation in the rotation direction R1. The connector CN connected to the pump 160 as described above may be coupled to the body 141.

In addition, the needle ND is coupled to a side of the body 141 opposite to the button 120, and the needle ND is connected to the connector CN and fluidically communicates with the tube TU. As shown in FIG. 6, while embodiments are not so limited, the needle ND in the illustrated embodiment is located substantially at the center of and protruding from a bottom surface 149 of the body 141.

A support wall 145 may stand in the Z-axis direction on a portion of the body 141 opposite a portion to which the connector CN is coupled. The support wall 145 may be formed in a circumferential direction along an edge of the body 141 to prevent the needle holder 140 from leaning to one side under the influence of tension of the tube TU, and the support wall 145 may function as a guide allowing the needle holder 140 to linearly move in an insertion direction K of the needle ND.

A second coupling portion 142 may be provided on a surface of the body 141 facing the button 120.

The second coupling portion 142 is configured to couple with the first coupling portion 125 (described above with respect to, e.g., FIG. 4), and may include a first coupling protrusion 142*a* and a second coupling protrusion 142*b* that protrude toward the button 120 and are spaced apart from each other. The first coupling protrusion 142*a* and the second coupling protrusion 142*b* of the second coupling portion 142 may be of a suitable type, as long as the first coupling protrusion 142*a* and the second coupling protrusion 142*b* can engage with the first coupling portion 125 as the button 120 is pressed by a user and can transmit rotational force of the button 120 to the needle holder 140 when the button 120 is rotated by the user. For example, when the first coupling portion 125 and the second coupling portion 142 are coupled to each other, the gap 125*c* between the first coupling protrusion 125*a* and the second coupling protrusion 125*b* of the first coupling portion 125 may be located between the first coupling protrusion 142*a* and the second coupling protrusion 142*b* of the second coupling portion 142. In this manner, the first coupling portion 125 and the second coupling portion 142 may engage with each other.

In addition, the first coupling portion 125 may be inserted into an end of the spring 130 shown in FIG. 2, and the second coupling portion 142 may be inserted into the other end of the spring 130, such that the spring 130 may be fixed between the button 120 and the needle holder 140. The spring 130 may be coupled between the button 120 and the needle holder 140 in a state in which the spring 130 is compressed to some degree. However, the location and configuration of the spring 130 is not limited thereto. For example, the spring 130 may be located between the button 120 and the needle holder 140 in a normal state in which the spring 130 is not compressed unless the button 120 is pressed by a user.

The needle holder 140 may include first supports 146 and guiding recesses 144.

In a first state in which the needle holder 140 is not rotated, the first supports 146 may be supported by guiding members 155 which will be described later (refer to FIG. 10) and may thus be spaced apart from the base 151 of the second casing 150 to some degree. That is, in the first state, the needle holder 140 may be spaced apart from the base 151 in the Z-axis direction.

The guiding recesses 144 may be adjacent to the first supports 146. As shown in FIGS. 5 and 6, the guiding recesses 144 may be next to the first supports 146 in the opposite direction of the rotation direction R1. The guiding recesses 144 may be formed by cutting off predetermined widths from the body 141 such that the guiding recesses 144 may penetrate the body 141 in the insertion direction K of the needle ND, for example, in the Z-axis direction in the drawings. In the second state in which the needle holder 140 has been rotated, the guiding members 155 (described later) may pass through the guiding recesses 144. That is, in the second state, the guiding members 155 are inserted into the guiding recesses 144, and the needle holder 140 may be slid by the spring 130 in the insertion direction K of the needle ND.

The first supports 146 may include support recesses 146*a* formed in an insertion-direction (K) surface of the body 141 in a recess shape having a predetermined depth in the Z-axis direction. The support recesses 146*a* may be connected to the guiding recesses 144, and support stoppers 146*b* may be between the support recesses 146*a* and the guiding recesses 144. The support stoppers 146*b* may be provided in a protrusion shape protruding in a direction opposite the direction in which the support recesses 146*a* are formed. In the first state, the guiding members 155 (described later) are supported in the support recesses 146*a*, and when the needle holder 140 is switched from the first state to the second state, that is, when the needle holder 140 is rotated in the rotation direction R1, the support stoppers 146*b* may provide resistance to the rotation to some degree. Therefore, when a user rotates the button 120 with a force greater than the resistance, the needle holder 140 is rotated in the rotation direction R1.

Still referring to FIGS. 5 and 6, in an embodiment, the second sensing member 183*b* may be installed on the needle holder 140. The second sensing member 183*b* may be located on an edge of the bottom surface 149 of the body 141. The second sensing member 183*b* is configured, in conjunction with the first sensing member 183*a* (FIG. 2), to sense whether the needle holder 140 is moved toward the base of the second casing 150 and adjacent to the needle penetration hole. The second sensing member 183*b* is provided in such a manner that when the needle holder 140 is adjacent to the needle penetration hole, the second sensing member 183*b* may make contact with the first sensing member 183*a* (FIG. 2). The second sensing member 183*b* may have a protruding shape for contact with the first sensing member.

The second sensing member 183*b* may include a conductive material. However, the second sensing member 183*b* is not limited thereto. That is, the second sensing member 183*b* may be of any type as long as the second sensing member 183*b* can sense, upon contacting the first sensing member 183*a* connected to the controller, whether the needle holder 140 is adjacent to the needle penetration hole. However, embodiments are not so limited. In other embodiments, the second sensing member 183*b* does not physically or electrically connect to the controller 180 through the first sensing member 183*a*. For example, the second sensing member 183*b* may be grounded.

Figure 7:
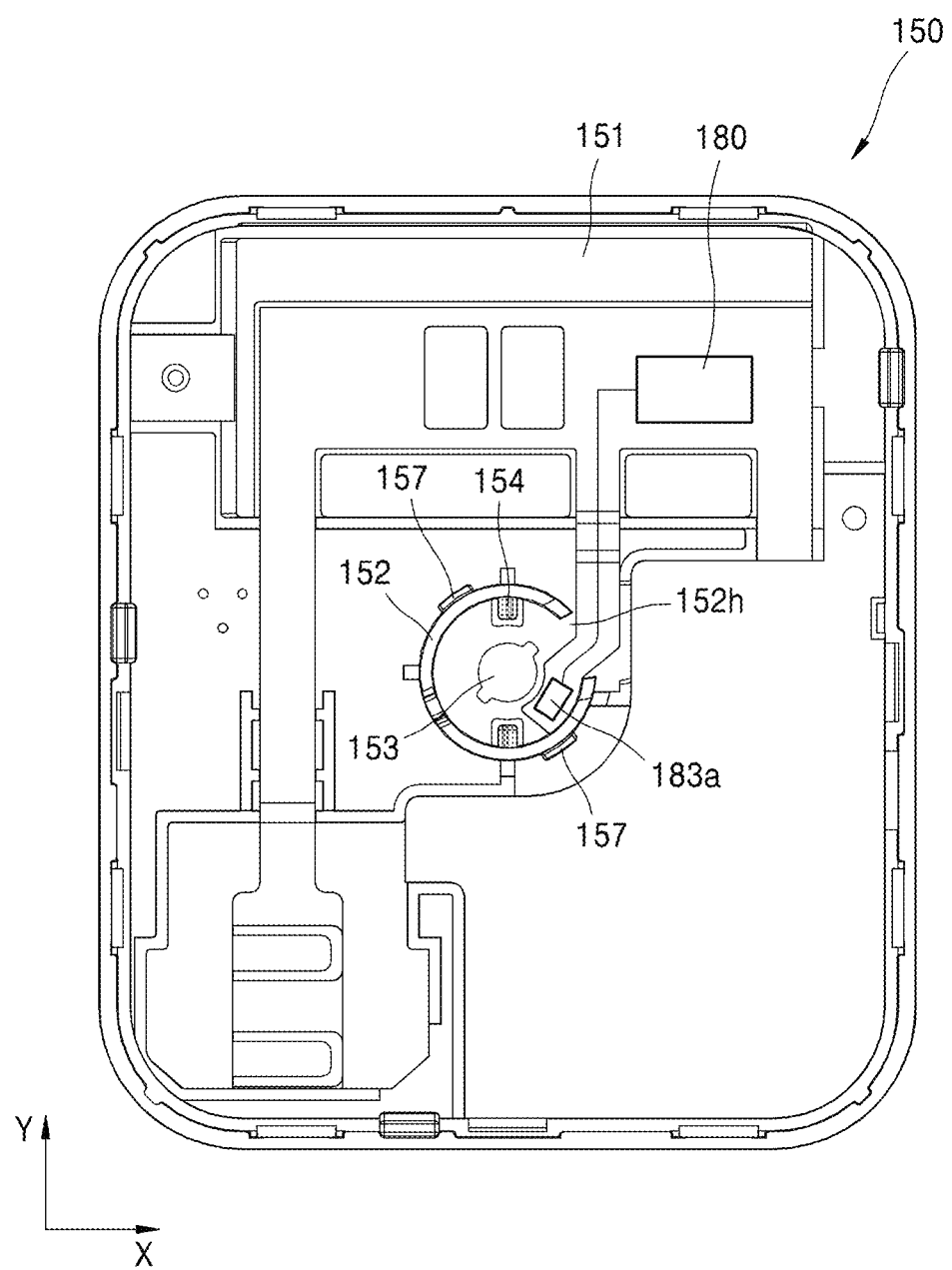
FIG. 7 is a plan view illustrating a second casing according to an embodiment.
Figure 8:
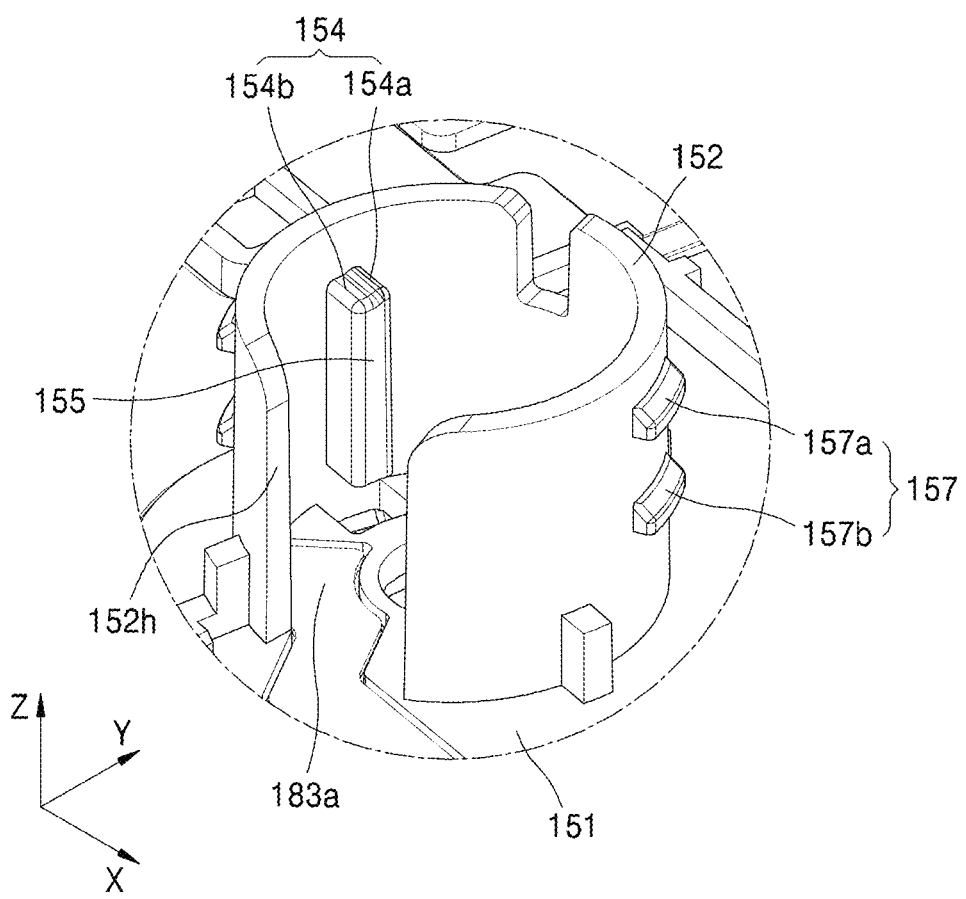
FIG. 8 is a partial perspective view illustrating the second casing illustrated in FIG. 7.

FIG. 7 is a plan view illustrating the second casing 150 according to an embodiment, and FIG. 8 is a partial perspective view illustrating a portion of the second casing 150.

The second casing 150 configured to be coupled to the first casing 110 may include the base 151. The base 151 may be part of the second casing 150, or may be separately formed and coupled to a bottom of the second casing 150.

The base 151 may include the needle penetration hole 153 approximately in a center portion thereof such that the needle may pass through the needle penetration hole 153.

A guide wall 152 having an approximately cylindrical shape may be formed around the needle penetration hole 153. The guide wall 152 may protrude from the base 151 toward the first casing in the Z-axis direction.

In the X-Y plane of FIG. 7, the outer diameter of the guide wall 152 may be less than the inner diameter of the lateral side 123 of the button 120 (FIGS. 2,3,4). Thus, when the button 120 is pressed, the lateral side 123 of the button 120 may be located outside the guide wall 152, and thus the button 120 may linearly slide along the guide wall 152 toward the needle holder 140, that is, in the needle insertion direction K.

As shown in FIG. 8, a cut recess 152*h* may be formed in a portion of the guide wall 152 from the base 151 to an end portion opposite the base 151. The connector CN of the needle holder 140 may pass through the cut recess 152h.

The guiding members 155 may be provided on an inner surface of the guide wall 152. The guiding members 155 may extend in the needle insertion direction K, for example in the Z-axis direction, and may have a rail shape. In the above-described second state, the guiding members 155 are inserted into the guiding recesses 144, and the needle holder 140 may slide along the guiding members 155 in the insertion direction K.

Second supports 154 may be formed on ends of the guiding members 155, e.g., on ends of the guiding members 155 facing the first casing 110. The second supports 154 may be configured to support the first supports 146 (FIG. 5) in the above-described first state. As shown in FIG. 8, each of the second supports 154 may include a first support portion 154a and a a support portion 154b. The first support portion 154a and the second support portion 154b of the second supports 154 may be connected to each other. In the rotation direction R1 of the needle holder, the first support portion 154a may be located downstream, and the second support portion 154b may be located upstream. In this case, since the first support portion 154a is more adjacent to the button 120 than the second support portion 154b, when the needle holder 140 is rotated in the rotation direction R1, a predetermined amount of resistance to the rotation may be provided. Therefore, when a user rotates the button 120 with a force greater than the resistance, the needle holder 140 is rotated in the rotation direction R1.

Stoppers 157 may be formed on an outer surface of the guide wall 152. The stoppers 157 may be protrusions protruding from the outer surface of the guide wall 152 in parallel with an X-axis, and as shown in FIG. 8, the stoppers 157 may extend in X-Y planes along an outer circumferential surface of the guide wall 152.

The stoppers 157 are provided to restrict sliding of the button 120 in the Z-axis direction. Each of the stoppers 157 may include a first stopper 157a and a second stopper 157b. The first and second stoppers 157a and 157b may be inserted into the coupling openings 127 of the button 120 shown in FIGS. 3 and 4, and since the coupling bands 123a are caught on the first and second stoppers 157a and 157b, the button 120 may not be separated in the opposite direction of the insertion direction K. The first stoppers 157a are coupled to the coupling openings 127 before the button 120 is pressed, and the second stoppers 157b are coupled to the coupling openings 127 when the button 120 is pressed.

In an embodiment, the first sensing member 183a may be further installed on the second casing 150. The first sensing member 183a may be installed on an FPCB, and the FPCB may be coupled to the base of the second casing 150. The first sensing member 183a may be electrically connected to the controller 180 through the circuit of the FPCB. In the drawings, the controller 180 and the first sensing member 183a are illustrated as being installed on the same FPCB. However, the present disclosure is not limited thereto. For example, the controller 180 may be installed on a circuit board different from the FPCB on which the first sensing member 183a is installed, and may be electrically connected to the first sensing member 183a.

The first sensing member 183a may be adjacent to the needle penetration hole 153, and to this end, the first sensing member 183a may extend to an inner side of the guide wall 152. That is, the first sensing member 183a may extend to the inner side of the guide wall 152 through a cut portion of the guide wall 152 formed to allow the connector CN to pass therethrough and is then located at a position adjacent to the needle penetration hole 153.

Figure 9:
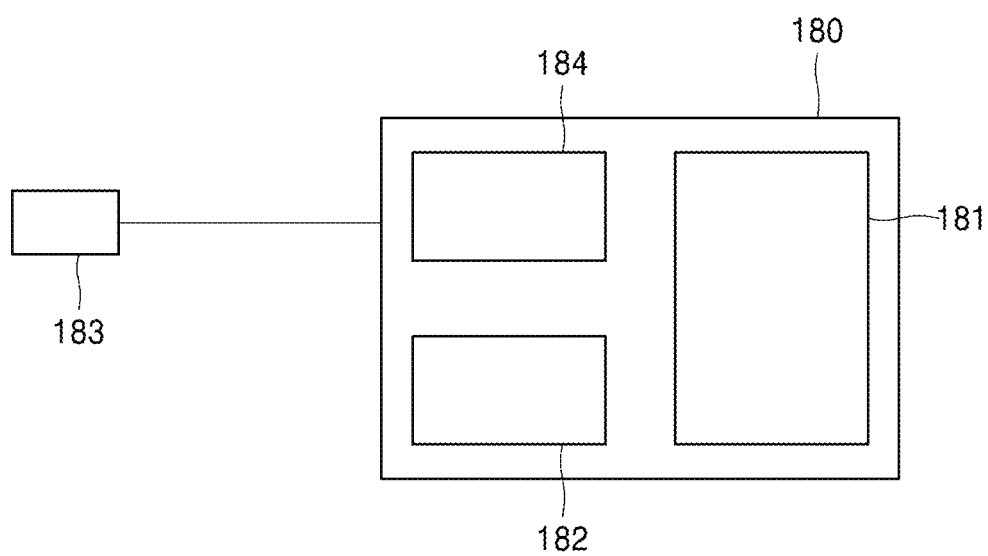
FIG. 9 is a block diagram schematically illustrating a sensor and a controller, according to an embodiment.

FIG. 9 is a block diagram schematically illustrating the sensor 183 and the controller 180 according to an embodiment.

According to the embodiment, the sensor 183 is provided as described above to sense whether the needle holder 140 is adjacent to the needle penetration hole 153 and may be electrically connected to the controller 180.

As described above, the controller 180 is electrically connected to the pump to control injection of the chemical fluid through the needle and may determine, using the sensor 183, whether the needle holder is adjacent to the needle penetration hole 153 (FIG. 7).

According to the illustrated embodiment, the controller 180 may include a first processor 181 and a second processor 182. The first processor 181 may control injection of the chemical fluid through the needle by controlling the pump. The second processor 182 determines, using the sensor 183, whether the needle holder is adjacent to the needle penetration hole 153, and upon determining that the needle holder is adjacent to the needle penetration hole, or in sufficient proximity thereto, the second processor 182 controls the first processor 181 to inject, e.g., initiate the injection of, the chemical fluid. Therefore, if the needle holder 140 is not adjacent to the needle penetration hole 153, the chemical fluid may not be injected even though a user performs a manipulation to inject the chemical fluid.

As described herein, the needle holder 140 being adjacent to the needle penetration hole 153 refers to a state or a configuration in which the needle sufficiently protrudes outward from the second casing 150, and may include a state or a configuration in which the needle is inserted into the body of a patient. Therefore, when it is sensed that the needle holder 140 is adjacent to the needle penetration hole 153, the second processor 182 determines that the needle is sufficiently inserted into the body of a patient and allows injection of the chemical fluid using the first processor 181. Therefore, when the needle is not sufficiently inserted into the body of a patient, injection of the chemical fluid does not occur, thereby preventing problems such as leakage of the chemical fluid or failure of chemical fluid injection into a target position.

The first and second processors 181 and 182 are not limited to being separate elements. For example, the first and second processors 181 and 182 may be a processor and/or a storage medium for storing and executing a program, or may be partitioned regions of a processor and/or a storage medium for executing separate sections of a program.

In another embodiment, the controller 180 may further include an alarm device 184.

The alarm device 184 may be electrically connected to the sensor 183 and may generate an alarm when the needle holder 140 is adjacent to the needle penetration hole 153. The alarm device 184 may include a light emitting device capable of emitting light as an alarm. And/or the alarm device 184 may include a micro-speaker device capable of generating a sound as an alarm. And/or the alarm device 184 may include a display device capable of displaying an alarm screen.

Although FIG. 9 illustrates a configuration in which the alarm device 184 is included in the controller 180. However, embodiments are not limited thereto. For example, the alarm device 184 may be configured as a separate element.

The alarm device 184 may be electrically connected to the first processor 181 and/or the second processor 182 in addition to being electrically connected to the sensor 183, and thus a user may be provided with alarms regarding other operations as well as an alarm regarding the sensing operation of the sensor 183.

The chemical fluid injection device 100 having the above-described configuration may be operated according to an embodiment as follows: when a user presses the button 120 in a state in which the user places an outer surface of the second casing 150 on a target area, e.g., a target area of a patient's body, for which the chemical fluid injection device 100 will be used. As described above, the button 120 and the needle holder 140 are coupled to each other. As the user rotates the button 120, the needle holder 140 is slid by the elasticity of the spring 130 in the insertion direction K of the needle ND, and thus the needle ND is momentarily inserted into the target area. In this case, when the button 120 is pressed, the spring 130 may be sufficiently compressed, and thus the needle ND may be momentarily inserted more effectively by the elasticity of the spring 130. Owing to this momentary insertion of the needle ND, patients may feel minimal pain and fear. In this case, whether the needle ND sufficiently protrudes after passing through the needle penetration hole 153 may be easily determined by sensing whether the needle holder 140 is adjacent to the needle penetration hole 153, that is, by sensing whether the needle holder 140 is brought into contact with a portion of the second casing 150 around the needle penetration hole 153. Thus, the user may inject the chemical fluid with an exact timing without loss of the chemical fluid and may not hesitate to insert the needle because of fear of needle insertion.

Figure 10A:
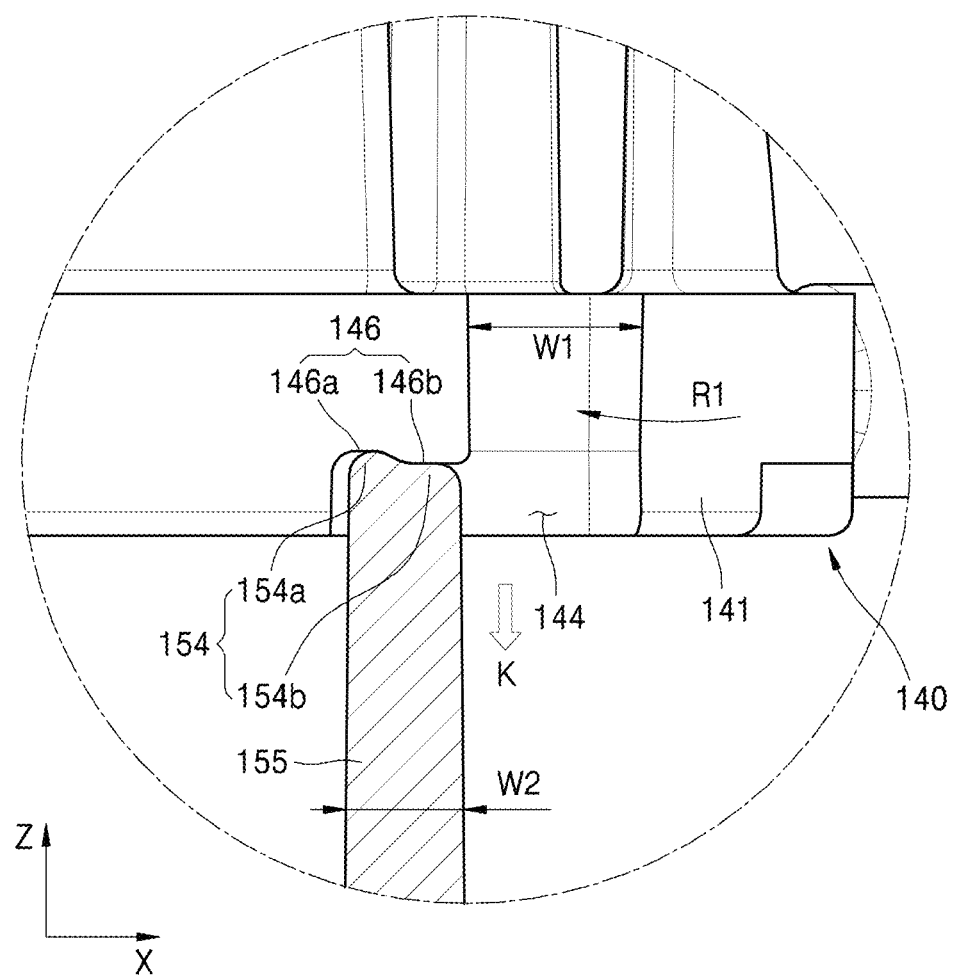
FIGS. 10A and 10B are views illustrating the needle holder and a guiding member respectively in a first state and a second state.
Figure 10B:
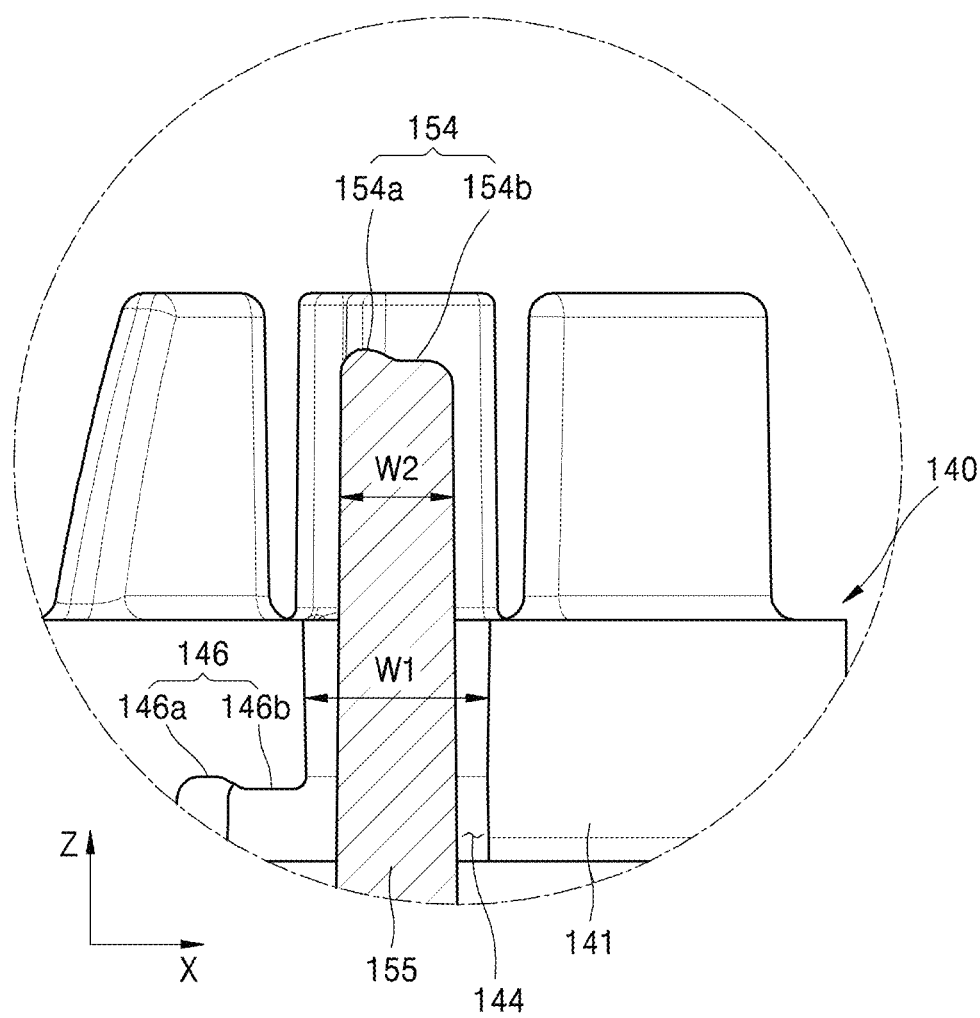

In an embodiment, for example, as shown in FIG. 10A, the needle holder 140 is spaced apart from the base 151 of the second casing 150 in the first state in which the needle holder 140 is not rotated. In this state, the needle is not yet inserted into the body of a patient. In the first state, the first supports 146 of the needle holder 140, and the second supports 154 of the guiding members 155 may be in contact with each other and supported by each other. In this case, according to an embodiment, the first supports 146 and the second supports 154 may have mutually engaging structures. Thus, the support recesses 146a and the second-first support portions 154a may make contact with each other, and the support stoppers 146b and the second-second support portions 154b may make contact with each other. Therefore, the needle holder 140 supported on end portions of the guiding members 155 may be more stably maintained in the first state.

When the needle holder 140 is rotated in the rotation direction R1 as the user presses the button 120, since the support stoppers 146b and the second-first support portions 154a are relatively moved against each other, resistance to the rotation of the needle holder 140 may be provided. If the user rotates the button 120 with a force greater than the resistance, and thus rotational force greater than the resistance is applied to the needle holder 140, the support stoppers 146b are moved over the second-first support portions 154a, and thus the guiding members 155 are introduced into the guiding recesses 144.

The guiding recesses 144 and the guiding members 155 respectively have a first width W1 and a second width W2 in the X-axis direction. The first width W1 may be greater than the second width W2 such that the guiding members 155 may be smoothly inserted into the guiding recesses 144.

When the needle holder 140 is completely rotated to the second state as the user rotates the button 120 as described above, as shown in FIG. 10B, the needle holder 140 is driven toward the base 151 of the second casing 150 as being slid along the guiding members 155 in a state in which the guiding members 155 are inserted in the guiding recesses 144, and thus the needle ND is inserted into the body of a patient.

Here, the needle holder is driven toward the base as force is momentarily exerted by compression of the spring, and thus, the needle coupled to the needle holder will be momentarily inserted into the body of a patient.

In the chemical fluid injection device of the embodiment, the needle holder includes the first supports 146, and the guiding members 155 include the second supports 154, to provide resistance to rotation of the needle holder and induce a user to apply rotation force greater than the resistance to the button. However, this is a non-limiting example of the present disclosure. That is, it is not definitely necessary to provide resistance to rotation of the needle holder, and the scope of the present disclosure may include a configuration in which the needle holder is rapidly slid by elasticity of the spring as the needle holder is rotated by a user, and thus the needle is momentarily insertable into the body of a patient.

In another embodiment, the chemical fluid injection device may further include the needle cover assembly to protect the needle before the needle is used by a user.

Figure 11:
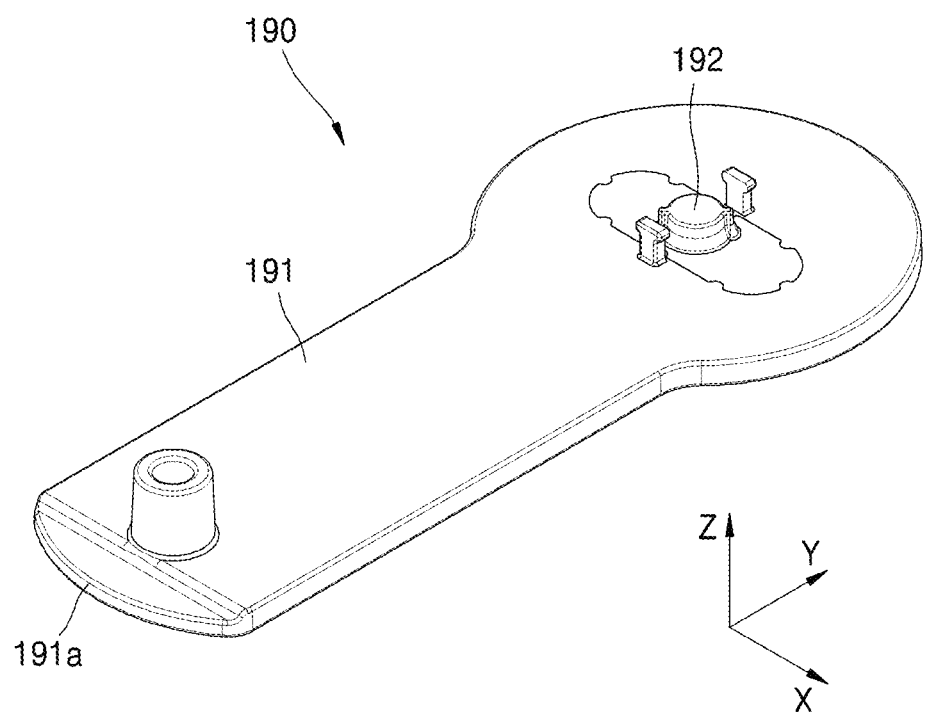
FIG. 11 is a perspective view illustrating a needle cover assembly, according to an embodiment.

FIG. 11 is a perspective view illustrating the needle cover assembly 190 of the embodiment.

The needle cover assembly 190 may include a cover plate 191, and the cover plate 191 may be a flat plate. An end of the cover plate 191 may function as a handle 191a such that a user may separate the needle cover assembly 190 from the casing using the handle 191a.

The needle cover assembly 190 may include a needle cover 192, and the needle cover 192 may be inserted into the needle penetration hole 153 provided in the base 151 of the second casing 150. Although not shown in the drawings, the needle cover 192 may include a closed space, and a tip of the needle may be partially inserted into the closed space. The closed space may include a portion including a material allowing air to pass therethrough but not allowing liquid to pass therethrough, or the closed space may include a portion having a variable volume. Thus, when a user performs priming to discharge air from the inside of the needle and/or the inside of the tube before use, the chemical fluid may not be discharged to the outside.

Embodiments of the present disclosure have been described with reference to the accompanying drawings for illustrative purposes only, and it will be understood by those of ordinary skill in the art that various changes and equivalent other embodiments may be made. Therefore, the scope and spirit of the present disclosure should be defined by the following claims.

Embodiments of the present disclosure has various commercial applications, including various chemical fluid injection devices for injecting a chemical fluid into the body of a patient, such as insulin injection devices

What is claimed is:

1. A chemical fluid injection device comprising:
    a casing including a needle penetration hole;
    a button exposed outside the casing;
    a needle holder located in the casing and configured to be coupled to a needle, the needle holder facing the needle penetration hole and configured to be driven toward the needle penetration hole by actuation of the button;
    a spring between the button and the needle holder;
    a guiding member provided in the casing and configured to selectively support the needle holder;

a sensor located in the casing and configured to sense whether the needle holder is adjacent to the needle penetration hole; and a controller electrically connected to the sensor;

wherein the needle holder is:
- configured to be driven toward the needle penetration hole by elasticity of the spring by activation of the button, and
- configured to be rotatable by rotation of the button by a user, and wherein the needle holder comprises:
- a first support supported by the guiding member in a first state where the needle holder is not rotated, and
- a guiding recess configured such that support with respect to the guiding member is released from the first state in a second state where the needle holder has been rotated and accordingly the needle holder receives elasticity of the spring.

2. The chemical fluid injection device of claim 1, wherein the sensor comprises:
- a first sensing member adjacent to the needle penetration hole; and
- a second sensing member coupled to the needle holder and facing the first sensing member.

3. The chemical fluid injection device of claim 1, further comprising an alarm device electrically connected to the sensor and configured to generate an alarm when the needle holder is adjacent to the needle penetration hole.

4. The chemical fluid injection device of claim 1, wherein the controller comprises:
- a first processor configured to control injection of a chemical fluid through the needle; and
- a second processor configured to determine, using the sensor, whether the needle holder is adjacent to the needle penetration hole, and to cause the injection of the chemical fluid using the first processor when the needle holder is adjacent to the needle penetration hole.

5. A chemical fluid injection device comprising:
- a casing including a base in which a needle penetration hole is formed;
- a needle holder located in the casing and configured to be coupled to a needle, the needle holder being configured to be driven toward the needle penetration hole, and configured to be rotatable by rotation of a button exposed outside the casing by a user;
- a guiding member provided in the casing and configured to selectively support the needle holder;
- a sensor located in the casing and configured to sense whether the needle holder is adjacent to the needle penetration hole; and
- a controller electrically connected to the sensor;

wherein the needle holder is apart from the base in a first state and is adjacent to the needle penetration hole in a second state;

wherein the controller is:
- configured to determine whether the needle holder is adjacent to the needle penetration hole in the second state, and
- configured to control a chemical fluid to be injected through the needle only when the needle holder is adjacent to the needle penetration hole;

wherein the needle holder is configured to be rotatable by rotation of a button; and wherein the needle holder comprises:
- a first support supported by the guiding member in a first state where the needle holder is not rotated, and
- a guiding recess adjacent to the first support and configured such that the guiding member passes through the guiding recess from the first state in a second state where the needle holder has been rotated and accordingly support with respect to the guiding member is released.

6. The chemical fluid injection device of claim 5, wherein the sensor comprises:
- a first sensing member adjacent to the needle penetration hole; and
- a second sensing member coupled to the needle holder and facing the first sensing member.

7. The chemical fluid injection device of claim 5, further comprising an alarm device electrically connected to the sensor and configured to generate an alarm when the needle holder is adjacent to the needle penetration hole in the second state.

8. The chemical fluid injection device of claim 5, wherein the controller comprises:
- a first processor configured to control injection of the chemical fluid through the needle; and
- a second processor configured to perform the injection of the chemical fluid using the first processor when the needle holder is adjacent to the needle penetration hole in the second state.

9. The chemical fluid injection device of claim 5, further comprising a spring configured to support the needle holder, wherein the needle holder is configured to be driven toward the needle penetration hole by elasticity of the spring when the needle holder is switched from the first state to the second state.

* * * * *

UNITED STATES PATENT AND TRADEMARK OFFICE
CERTIFICATE OF CORRECTION

PATENT NO. : 10,786,623 B2  Page 1 of 1
APPLICATION NO. : 16/128323
DATED : September 29, 2020
INVENTOR(S) : Jesse Jaejin Kim et al.

It is certified that error appears in the above-identified patent and that said Letters Patent is hereby corrected as shown below:

In the Specification

In Column 6, Line 34, delete "FIGS. 5 and 5)" and insert --FIGS. 5 and 6--.

In Column 9, Line 17 (Approx.), delete "a a" and insert --a--.

In Column 12, Line 56, delete "devices" and insert --devices.--.

In the Claims

In Column 14, Line 13 (Approx.), Claim 5, delete "button; and" and insert --button by a user; and--.

Signed and Sealed this
Eighth Day of December, 2020

Andrei Iancu
*Director of the United States Patent and Trademark Office*